United States Patent
Ikonen et al.

(10) Patent No.: US 10,608,886 B2
(45) Date of Patent: Mar. 31, 2020

(54) WIRELESS MEDICAL BODY AREA NETWORK AND A METHOD FOR MANAGING WIRELESS DEVICES FOR THE SAME

(71) Applicant: GENERAL ELECTRIC COMPANY, Schenectady, NY (US)

(72) Inventors: Emma Elina Ikonen, Helsinki (FI); Kristian Matti Karru, Helsinki (FI); Otto Valtteri Pekander, Helsinki (FI)

(73) Assignee: General Electric Company, Schenectady, NY (US)

( * ) Notice: Subject to any disclaimer, the term of this patent is extended or adjusted under 35 U.S.C. 154(b) by 60 days.

(21) Appl. No.: 15/540,087

(22) PCT Filed: Sep. 17, 2015

(86) PCT No.: PCT/US2015/050696
§ 371 (c)(1),
(2) Date: Jun. 27, 2017

(87) PCT Pub. No.: WO2016/108964
PCT Pub. Date: Jul. 7, 2016

(65) Prior Publication Data
US 2017/0372024 A1   Dec. 28, 2017

(30) Foreign Application Priority Data
Dec. 31, 2014 (GB) .................................. 1423369.6

(51) Int. Cl.
*G06F 19/00* (2018.01)
*H04L 12/24* (2006.01)
(Continued)

(52) U.S. Cl.
CPC .............. *H04L 41/12* (2013.01); *G06F 19/00* (2013.01); *G16H 40/63* (2018.01); *H04W 84/20* (2013.01); *Y02A 90/26* (2018.01)

(58) Field of Classification Search
None
See application file for complete search history.

(56) References Cited

U.S. PATENT DOCUMENTS 9,467,942 B2 * 10/2016 Watanabe ......... H04W 52/0219
10,244,542 B2 * 3/2019 Athani .................. H04W 76/10
(Continued)

FOREIGN PATENT DOCUMENTS

EP          1833197 A1    9/2007
WO     2010018516 A1    2/2010
(Continued)

OTHER PUBLICATIONS

International Search Report and Written Opinion for PCT/US2015/050696, dated Dec. 15, 2015, 14 pages.
(Continued)

*Primary Examiner* — Steve R Young
(74) *Attorney, Agent, or Firm* — Andrus Intellectual Property Law, LLP

(57) ABSTRACT

A method for managing wireless devices in a wireless medical body area network, MBAN, comprises configuring the wireless MBAN based on all wireless devices of the MBAN comprising at least one sensor and at least one hub, by sharing identification data, battery status, and communication performance between wireless devices of the wireless MBAN; providing a plurality of the wireless devices with at least short range communication and long range communication; and configuring a first wireless device of the wireless MBAN as a master depending on battery status and communication performance. Thereafter, the method comprises
(Continued)

configuring a second wireless device of the wireless MBAN as a new master if the battery status and communication performance of the master drops below that of the second wireless device; and routing data transfer within the wireless MBAN depending on the battery status and communication performance of the wireless devices of the wireless MBAN.

15 Claims, 3 Drawing Sheets

(51) Int. Cl.
*H04W 84/20* (2009.01)
*G16H 40/63* (2018.01)

(56) References Cited

U.S. PATENT DOCUMENTS

| | | | |
|---|---|---|---|
| 2007/0253345 A1 | 11/2007 | Habetha et al. | |
| 2011/0213216 A1* | 9/2011 | McKenna | A61B 5/0002 600/301 |
| 2013/0178150 A1 | 7/2013 | Park et al. | |
| 2013/0337749 A1* | 12/2013 | Wang | H04W 4/80 455/41.2 |
| 2014/0233458 A1* | 8/2014 | Georgescu | H04W 6/50 370/328 |
| 2014/0293852 A1* | 10/2014 | Watanabe | H04W 52/0219 370/311 |
| 2015/0115711 A1* | 4/2015 | Kouroussis | H02J 9/061 307/23 |
| 2018/0184360 A1* | 6/2018 | Cavalcanti | H04W 52/0261 |

FOREIGN PATENT DOCUMENTS

| | | |
|---|---|---|
| WO | 2012117320 A1 | 9/2012 |
| WO | 2012120427 A1 | 9/2012 |

OTHER PUBLICATIONS

Combined Search and Exam Report for corresponding GB Appln. No. 1423369.6, dated Jun. 16, 2015, 4 pages.

IEEE Standard for Local and Metropolitan Area Networks—Part 15.6: Wireless Body Area Networks, IEEE Computer Society, IEEE Standards Association, IEEE Std 802.15.6-2012, Feb. 29, 2012, 271 pages.

* cited by examiner

WIRELESS MEDICAL BODY AREA NETWORK AND A METHOD FOR MANAGING WIRELESS DEVICES FOR THE SAME

CROSS-REFERENCE TO RELATED APPLICATIONS

This application is a filing under 35 U.S.C. 371 of international application number PCT/US2015/050696, filed Sep. 17, 2015, which claims priority to GB application number 1423369.6, filed Dec. 31, 2014, the entire disclosures of each are hereby incorporated by reference.

TECHNICAL FIELD

The present disclosure relates to a wireless medical body area network (MBAN) and a method for managing the wireless MBAN. More particularly, the present disclosure relates to a wireless MBAN and routing data within the MBAN, and optionally to a second network.

BACKGROUND

Patients may be monitored with sensors connected by cables to a hub. The hub can connect to an infrastructure of a hospital. In this way a patient can be monitored. The network of sensors around one and the same patient and used for monitoring that patient together with the hub is called a medical body area network or MBAN for short. In this network the sensors send data to the hub and the hub send the data to the infrastructure of the hospital. Monitoring vital signs is an important part of patient care as the general or particular health of the patient is determined, in part, through measurement and interpretation of key physiological indicators. Parameters of patient health include blood pressure, haemoglobin saturation, and features of electrocardiogram (ECG).

However, the utilization of physiological instrumentation to obtain those measurements at bedside also possesses burdens to clinical environment. The presence of cables, catheters, and tubing connecting the patient and sensors to the instrumentation can diminish productivity and the quality of patient care. For example, rotating a patient to alleviate bedsores or ambulating about the room can be problematic if one is saddled with tethered devices. Procedural delays stemming from cable management also contribute to a greater percentage of time dedicated to routine, mundane tasks not directly related to treatment of the patient's illness.

Using a wireless MBAN is problematic because the sensors are not physically connected to each other or the hub, for example, it is difficult to know what devices are part of the wireless MBAN. With wireless applications the communication can be carried out without a physical connection and, for example, patients can be moved or care procedures can be done. A wireless system is typically constructed in a way that each body worn sensor communicates via a short range and low energy, medical body area network (MBAN) radio to the patient monitor or hub. At the same time, problems of connection reliability and compromised security to alarm critical conditions of the patient appear.

MBAN radio is a short range communication method with a typically range of up to 5 meters. This is enough when the patient is in bed and the host monitor or patient hub is located near the bed. However, it is possible that mobile patients can move out of the MBAN radio range while the personal hub device or patient monitor stays by the bed. In case a critical condition appears during the time the patient is out of the MBAN radio range, it may be crucial for the well-being of the patient that the alarms still appear on the bed-side monitor/hub.

The present MBAN requires each sensor of the MBAN to be connected to the hub. It is a problem to ensure such a connection. It is further a problem to manage an MBAN to ensure the well-being of the patient. It is a problem to optimise communication within a wireless MBAN and/or from the wireless MBAN to a second network. It is a problem to optimise power management of wireless devices of a wireless MBAN. It is a problem to find economically and technically adequate solutions.

SUMMARY

The present disclosure is directed to a wireless MBAN and a method for managing wireless devices in a wireless MBAN. This can be achieved by the features as defined by the independent claims. Further enhancements are characterized by the dependent claims. For this disclosure a medical body area network, MBAN, may be one or more sensors connected by cables or wirelessly to a hub. It may also include one or more sensors connected by cables or wirelessly to a sensor acting as a hub. The MBAN may be used in a hospital, at home, sport facility, or other place. The hub may connect to an infrastructure of a hospital, home, sport facility, or other place, such as the internet, telephone network, or other suitable infrastructure. In this way a patient can be monitored. The MBAN may be the network of sensors around one and the same patient and used for monitoring that patient together with the hub (or sensor).

In one embodiment, the present disclosure is directed to a method for managing wireless devices in a wireless medical body area network, MBAN. The method comprises configuring the wireless MBAN network based on all wireless devices of the medical body area network comprising at least one sensor and at least one hub, or a sensor acting as a hub, the configuring comprising sharing at least identification data, battery status, and communication performance between all wireless devices of the wireless MBAN; providing all wireless devices with at least short range communication and long range communication; and configuring a first wireless device of the wireless MBAN as a master of the wireless MBAN depending on the battery status and the communication performance. Thereafter, for managing the wireless devices in the wireless MBAN, the method comprises configuring a second wireless device of the wireless MBAN as a new master if the battery status and communication performance of the master drops below a predefined level of the battery status and communication performance of the second wireless device; and routing data transfer within the wireless MBAN depending on the battery status and communication performance of the wireless devices of the wireless MBAN.

In one embodiment, the present disclosure is directed to a wireless medical body area network, MBAN, comprising a plurality of wireless devices comprising at least one sensor and at least one hub. The plurality of wireless device being configured to share at least identification data, battery status, and communication performance between the plurality of wireless devices of the wireless MBAN; and each wireless device being configured for both short range communication and long range communication. The hub is configured as a master; and each wireless device is configured for routing data within the wireless MBAN and for selecting a new master within the wireless MBAN depending on the battery status and communication performance of each wireless device of the wireless MBAN.

In these embodiments, the master may be configured for communicating with a second network. The master may use long range wireless communication to communicate with the second network and/or the master may use a wired network, e.g. a cable, to communicate with the second network. The at least short range communication and long range communication all wireless devices may be at different frequencies.

In these embodiments, the wireless devices may communicate between each other only using short range communication. The at least one hub may be provided with a larger battery capacity compared with each sensor of the MBAN. In this way it has initially the better battery status and communication performance. One option for configuring a first wireless device of the wireless MBAN as a master of the wireless MBAN depending on the battery status and the communication performance, may be by selecting the wireless device that has the best battery status and/or the best communication performance.

At least according to one embodiment, the method and wireless MBAN is a more robust system, with backup data transfer capability still maintaining low energy solutions. Robustness of data transfer is important. At least one embodiment provides a smart and adaptive method to change communication method if needed and equalization of the battery consumption between wireless devices.

At least one of the above embodiments provides one or more solutions to the problems and disadvantages with the background art. Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

Figure 1:
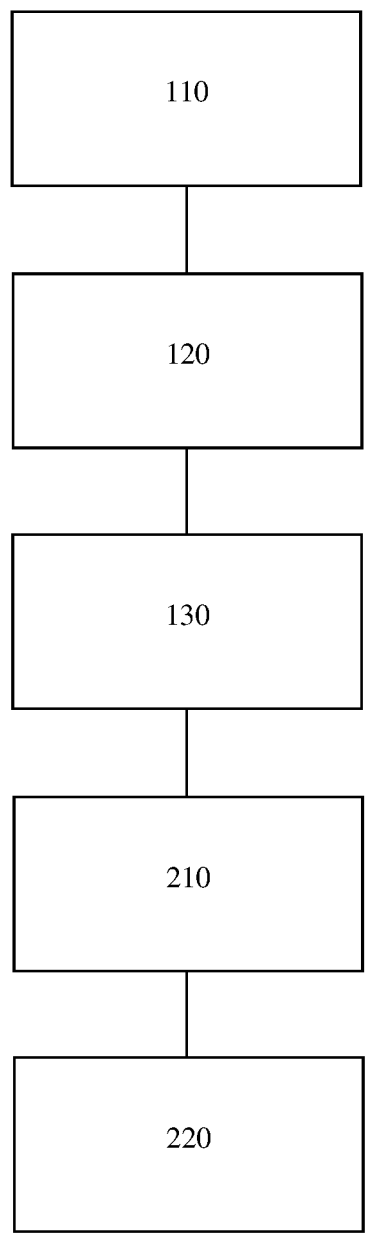
FIG. 1 shows a flow chart of a method according to an exemplary embodiment of the disclosure.

FIG. 1 shows a flow chart of a method according to an exemplary embodiment. The method is a method for managing wireless devices in a wireless medical body area network, MBAN. The wireless MBAN may be for a single patient and for all, or only some of, the wireless devices, such as sensors and one or more hubs (e.g. a monitor, master). The following method steps 110-130 may be taken in any order, but the first three steps may be for pairing, setting up, the wireless MBAN. These three steps 110-130 are therefor taken initially, and the steps 210-220 thereafter can be taken in any order.

A first step 110 may be configuring the wireless MBAN network based on all wireless devices of the medical body area network comprising at least one sensor and at least one hub, the configuring comprising sharing at least identification data, battery status, and communication performance between all wireless devices of the wireless MBAN. During this step of pairing, setting up the wireless MBAN for managing the wireless MBAN, a plurality of wireless devices may be connected to the wireless MBAN. The plurality of wireless devices may comprise one or more sensors and one or more hubs, monitors. The one or more hubs, monitors, may be one or more sensors acting as a hub or monitor. The sensors may be any kind of medical sensor, for example a reusable sensor or a disposable sensor, for example for blood pressure, oxygen level, features of electrocardiogram, etc. The hub may be a monitor and the wireless MBAN could comprise more than only one hub. The hub may have a further communication possibility with a second network and may also provide medical staff the possibility to read and monitor the different sensors within the wireless MBAN.

A second step 120 may be providing a plurality of the wireless devices with at least short range communication and long range communication. The plurality of devices may be all wireless devices, or all wireless devices in the wireless MBAN. These two communications may communicate at different frequencies. They may, for example, not operate within the same frequency ranges. The short range communication may be for example a MBAN radio of, for example, a maximum range of 5, or 4, or 3 meters. The short range communication may have low energy consumption, especially when compared with energy consumption of long range communication. Long range communication may for example be Wi-Fi radio, extending several times (e.g. 2, 3, 4, 5 times) that of the short range. The long range communication may have high energy consumption, especially when compared with energy consumption of short range communication. The short range communication and long range communication may therefore differ in the range they can communicate, the energy they consume or need, and by the frequency range. That the wireless MBAN has these two different possibility to communicate within the wireless MBAN and/or from the wireless MABN to a second network allows for an efficient and secure way of communicate, optimising communication and power management of the wireless MBAN and its devices.

A third step 130 may be configuring a first wireless device of the wireless MBAN as a master of the wireless MBAN depending on the battery status and the communication performance. When pairing, setting up, the wireless MBAN a master may be selected. This master may have the best battery status and/or the best communication performance A hub, for example a monitor, may have a larger battery with a better battery status than a smaller battery for a relatively small sensor. A hub may have, at least initially, a better communication performance because it may have short range and long range and wired communication. However, if the hub later on, or initially, is disconnected from the wireless MBAN, because for example the patient moves away from the hub, then another wireless device, for example a sensor or another hub, may take the place as a master, even initially when pairing, setting up the network.

These first three steps 110-130 may be taken in any order. After the first three steps 110-130 the method for managing the wireless devices in the wireless MBAN may comprise the following steps 210-220 taken in any order. The following steps 210-220 may thus be taken after pairing, setting up, the wireless MBAN with one or more wireless devices.

A fourth step 210 may be configuring a second wireless device of the wireless MBAN as a new master if the battery status and communication performance of the master drops below a predefined level of the battery status and communication performance of the second wireless device. Another wireless device, different from the wireless device initially set up as the master, may become a new, replacing, master. The first wireless device configured as the master may have a battery status and communication performance that is not acceptable or allows it to connect to a second network or to communicate with other wireless devices within the wireless MBAN. The second wireless device, for example a sensor or another hub, may have a better battery status and/or communication performance and this second wireless device then may become a new master of the wireless MBAN. A predefined level of the battery status and communication performance may, for example, be 20 percent of the battery capacity and/or a RSSI number describing the link strength drops below −70 dBm (IEEE 802.11). These values are only examples and any suitable predefined level may be used, for example any level from 1 to 99 percent, such as for example 5, 10, 15, 20, 25, 30, 35, 40, 45, or 50 percent, and for example any RSSI value of the signal strength, depending on equipment, 0 to max, such as for example 50, 55, 60, 65, 70, 75, 80, 85, 90 dBm.

A fifth step 220 may be routing data transfer within the wireless MBAN depending on the battery status and communication performance of the wireless devices of the wireless MBAN. The wireless devices, including the at least one sensor and the at least one hub may route, direct, data communication, transfer, within the wireless MBAN depending on their battery status and communication performance. For example, if one sensor can not communicate with the master, then that sensor may communicate with another sensor who in turn can communicate with the master. If the battery status does not allow for a wireless device to use the more energy demanding long range communication, then the data may be routed to another wireless device that has the battery status to allow long range communication. If the communication performance does not allow for a wireless device to use a certain communication, then a different communication possibility for that wireless device may be used, or the data may be routed to another wireless device that can provide the necessary communication. It may be a combination of the battery status and the communication performance that decides how data is routed.

Figure 2:
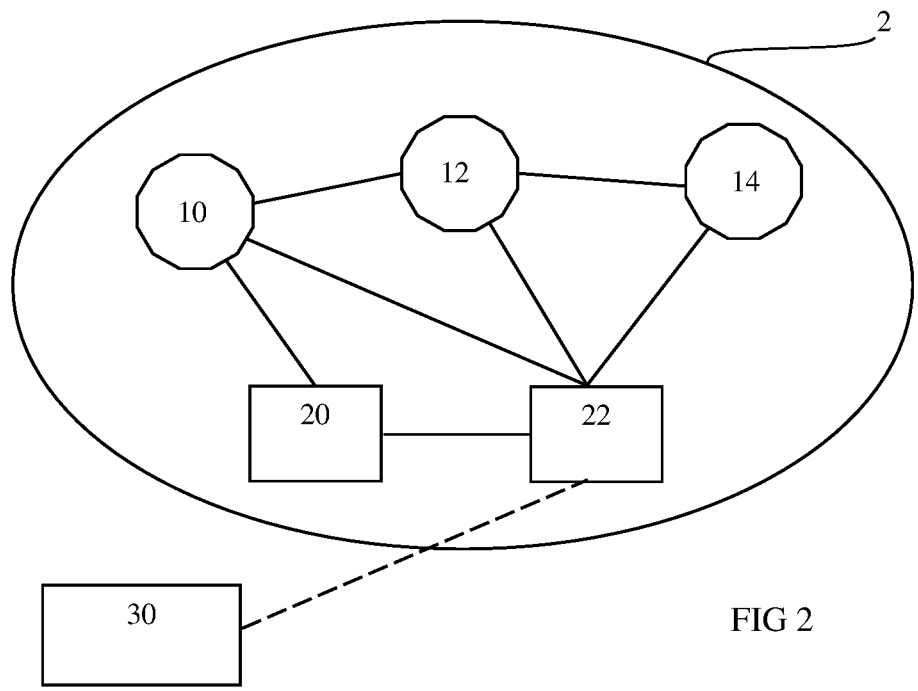
FIG. 2 is a diagrammatic illustration of a wireless MBAN according to an exemplary embodiment of the disclosure.
Figure 3:
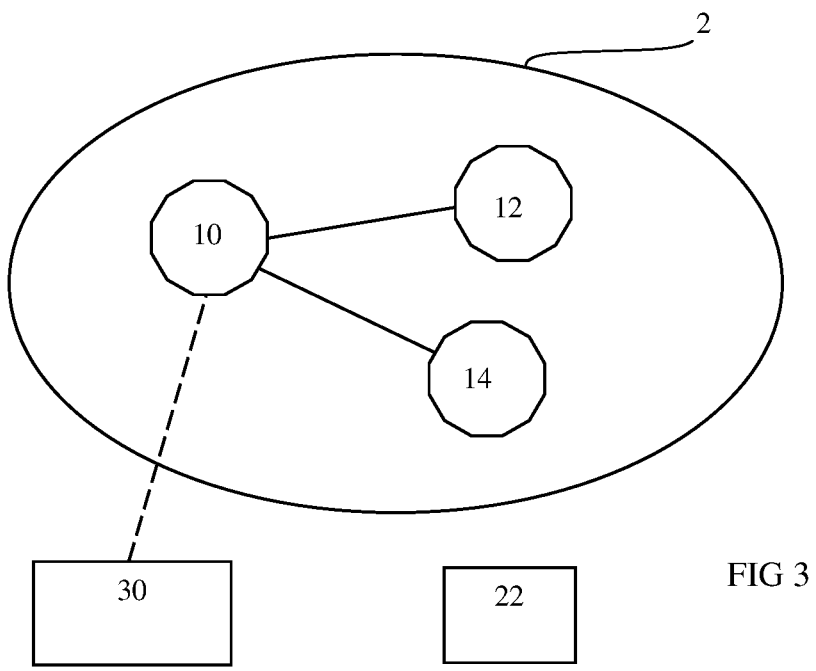
FIG. 3 is a diagrammatic illustration of a wireless MBAN according to an exemplary embodiment of the disclosure.
Figure 4:
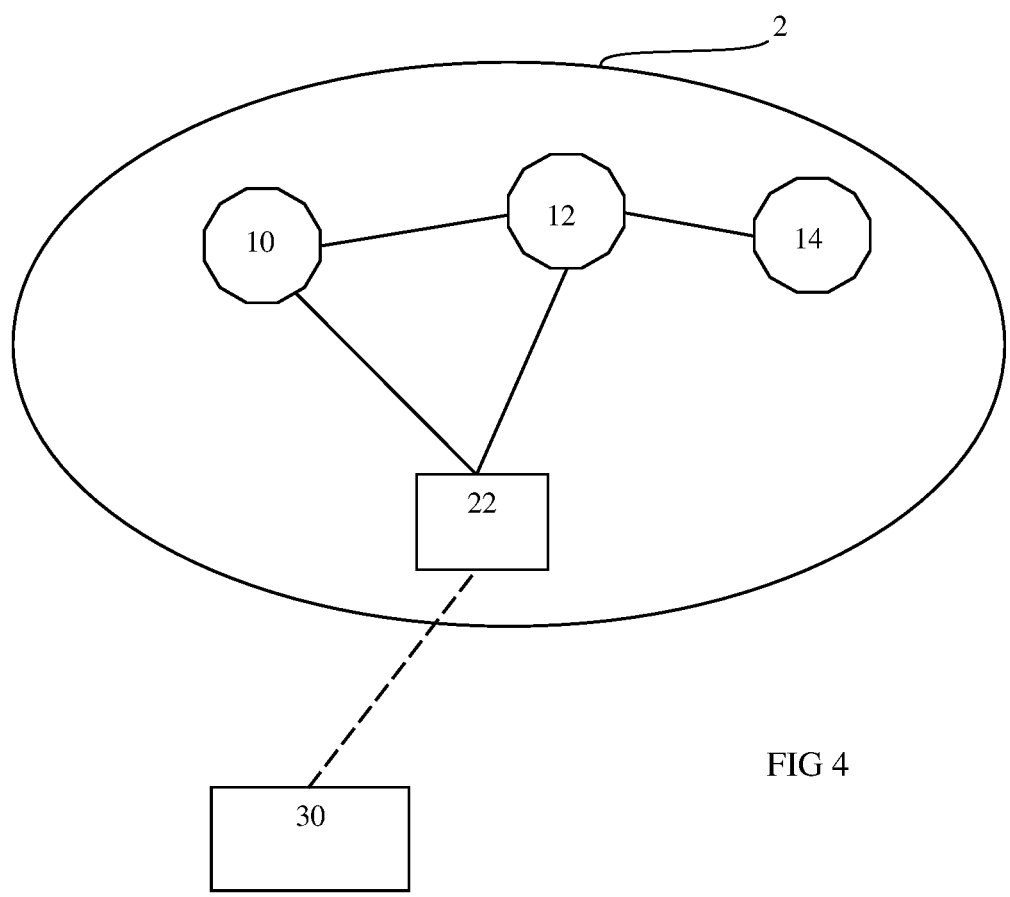
FIG. 4 is a diagrammatic illustration of a wireless MBAN according to an exemplary embodiment of the disclosure.

With reference to FIGS. 2 to 4, according to one embodiment, the master is configured for communicating with a second network 30. The second network 30 may belong to the infrastructure of a hospital. For example, the data collected by the wireless devices 10, 12, 14 of the wireless MBAN 2 may be routed to the second network 30 to be stored in the patient data storage. For example, an alarm triggered by the wireless devices of the wireless MBAN may be forwarded to the second network 30 to sound an alarm to the relevant caretakers.

According to one embodiment, the master may use long range communication to communicate with the second network 30. The long range communication may be wireless. According to one embodiment, the master may use a wired network to communicate with the second network 30. For example, the hub may be connected by wire to the infrastructure of a hospital.

As illustrated in FIG. 3, if the hub 22 can not communicate with the second network 30 or with the wireless devices of the wireless MBAN, then a second wireless device 10, for example a sensor, may become the master and communicate with the second network 30, for example wirelessly as indicated in FIG. 3 by the broken line from wireless device 10 to the second network 30. In this embodiment, the wireless device 10, for example a sensor 10, acts as the hub for the wireless MBAN.

According to one embodiment, the wireless devices 10, 12, 14, 20, 22 may communicate between each other only using short range communication. This saves battery because the short range communication uses less energy.

According to one embodiment, the method may comprise configuring the at least one hub with a larger battery capacity compared with each sensor of the MBAN. The hub 20, 22 may be a monitor that medical staff can use to monitor the different sensors within the wireless MBAN. Such a monitor may have a screen and may therefore require a battery with a larger battery capacity. Smaller wireless sensors attached to the patient may have a battery with a smaller battery capacity. Such a configuration of a wireless MBAN would provide a suitable network for optimising communication and power management within the wireless MBAN.

According to one embodiment, the configuration of a first wireless device of the wireless MBAN as a master of the wireless MBAN depending on the battery status and the communication performance, may comprise selecting the wireless device that has the best battery status and communication performance. The best battery status and the best communication performance may be a comparison and/or evaluation of the battery status and/or communication performance of all, or only some of, the wireless devices of the wireless MBAN. In this way the wireless MBAN may provide a secure way of communicate within the wireless MBAN and also between the wireless MBAN and the second network 30. According to one embodiment, a master of the wireless MBAN may be chosen based on a value calculated from battery status and/or communication performance. The best battery status and communication performance may give highest value and may be used for determining the master of the wireless MBAN. If the value drops on a predefined level below the battery status and communication performance of the second wireless device, second wireless device takes the master role. A predefined level of the battery status and communication performance may, for example, be 20 percent of the battery capacity and/or a RSSI number describing the link strength drops below −70 dBm (IEEE 802.11). These values are only examples and any suitable predefined level may be used, for example any level from 1 to 99 percent, such as for example 5, 10, 15, 20, 25, 30, 35, 40, 45, or 50 percent, and for example any RSSI value of the signal strength, depending on equipment, 0 to max, such as for example 50, 55, 60, 65, 70, 75, 80, 85, 90 dBm.

According to one embodiment, a wireless device, which can not communicate directly with the master, communicates via one or more wireless devices of the wireless MBAN with the master. This is for example illustrated in FIG. 4, where a wireless device 14 may for some reason not be able to communicate directly with the master 22. However, the wireless device 14 may be able to communicate with a wireless device 12, and this wireless device 12 may in turn be able to communicate with the master 22. In this way all data collected by the wireless devices 10, 12, 14 may be communicated to the master 22 and in turn to the second network 30.

In one embodiment, as shown for example in FIGS. 2-4, a wireless medical body area network, MBAN, comprises a plurality of wireless devices 10, 12, 14, 20, 22. The plurality of devices may comprise at least one sensor 10, 12, 14 and at least one hub 20, 22. The at least one hub may be a sensor acting as a hub. The plurality of wireless devices may be configured to share at least identification data, battery status, and communication performance between the plurality of wireless devices of the wireless MBAN. Each of the plurality of the wireless devices may be configured for both short range communication and long range communication. One hub of the at least one hub may be configured as a master. Each wireless device may be configured for routing data within the wireless MBAN and for selecting a new master within the wireless MBAN depending on the battery status and communication performance of each wireless device of the wireless MBAN. The plurality of devices can be all of the wireless devices of the wireless MBAN. By sharing only identification data, battery status, and communication performance between the plurality of wireless devices the overhead can be significantly reduced. The sharing may take place between each of the plurality of wireless devices. The short range communication and long range communication may be made at different frequencies. The short range communication and long range communication have been mentioned above, and the short range communication requires less energy when compared with the long range communication which requires more energy. For example, the long range communication requires about three times more energy than the short range communication. In other word, while the long range communication can last for example eight hours, the short range communication can last for example twenty-four hours on the same battery. Initially, the hub may be configured as the master, but as the battery status changes and/or the communication performance changes between the wireless devices, for example a wireless device can not communicate as required, a new master may be selected. This allows the wireless MBAN to be a robust network with an optimised communication and power management.

According to one embodiment, the master 22 may be configured for communicating with a second network 30. The master may be configured to use long range wireless communication to communicate with the second network 30. As an alternative, or addition, the master may be configured to use wired network to communicate with the second network 30.

According to one embodiment, the wireless devices 10, 12, 14, 20, 22 may be configured to communicate between each other only using short range communication. This would save the battery capacity for the wireless devices. The at least one hub may have a larger battery capacity compared with the battery capacity of each sensor.

According to one embodiment, a wireless device 14, which can not communicate directly with the master 22, is configured to communicate via one or more wireless devices 10, 12 of the wireless MBAN with the master 22. In this way the network achieves optimised communication. This is illustrated in FIG. 4.

The features described above and below relating to the method and the wireless MBAN can all be combined as long as it makes technical sense. They all serve to disclose at least one embodiment of the disclosure. What is described in relation to the method also discloses the wireless MBAN, and vice versa.

In the wireless MBAN 2 the wireless devices 10, 12, 14, 20, 22 are equipped with short and long range communication, for example working in different frequencies. Primarily all of the devices may communicate together via the short range communications as it is requires less power to operate. One device of the MBAN is chosen as a gateway or master 22 with the responsibility of taking care of longer range communication and/or wired to the infrastructure, e.g. a hospital network. The other devices within the MBAN 2 may send data via short range communication to the master. The wireless MBAN may be used in a hospital and may be constructed by strictly defined parameters with reduced overhead. The wireless MBAN may use more than one operation frequency and communication protocols in every single node, wireless device, making it even more robust. The wireless MBAN may be assigned to a certain patient and automated checks may be based on communication of the wireless devices and/or checking that each wireless device is constantly connected to the same patient.

The method and wireless MBAN disclosed allow a reduction of overhead within the network. The reduction of overhead data is useful within a wireless MBAN with limited battery capacity and efficient communication performance.

Turning to FIGS. 2-4 more in detail, three embodiments are illustrated. Each wireless device 10, 12, 14, 20, 22, for example body worn sensors 10, 12, 14 communicates point-to-point to the host monitor or hub 20, 22 device via low energy and low range MBAN radio protocol, a short range communication. The host master/monitor or hub sends the data from the sensors via wired or wireless network to, for example, an infrastructure of a hospital. There are numerous situations where this point-to-point MBAN communication might be compromised. Still alarms and measured patient data have to be transferred to the infrastructure. These situations may, for example, be host device failure; one or more sensors out of MBAN range for example under warming blanket etc.; a mobile patient is out of MBAN range; short range communication frequencies are suffering from extensive use or noise; etc.

According to one or more embodiments, all, or at least a plurality, of wireless devices 10, 12, 14, 20, 22 are part of a wireless MBAN connected to a single patient, where every wireless device knows at all times the device identification, connection status, and battery status of the other devices in the wireless MBAN, i.e. same community. One of the devices in the wireless MBAN is configured to act as a master 22 connection gateway to the infrastructure. The selection of the master device is based on battery status and communication performance, the best connection quality and battery capacity. When the wireless MBAN is set up initially, a host monitor or hub may have the best battery status and communication performance and may be selected as the master, collect the measurement data from the sensors and send the data to the infrastructure. This is illustrated in FIG. 2, where the wireless devices 10, 12, 14, 20, 22 are sensors 10, 12, 14 and hubs 20, 22. The wireless devices are part of the wireless MBAN 2. An example of how the wireless devices 10, 12, 14, 20, 22 can communicate with each other are illustrated by drawn lines between the wireless devices. The master, hub 22, can communicate with a second network 30 and this is illustrated by the broken line, for example by long range communication or wire.

When something goes wrong and the master (primary gateway) loses its ability to send the data, a new (emergency) master is chosen within the wireless MBAN devices to act as the gateway. Long range communication consumes more power than short range communication and sensors may have a limited battery capacity. The emergency master role can be swapped to another device of the wireless MBAN community when the battery capacity of the emergency master drops. By chancing the long range communication master device role the overall battery capacity is used more evenly and all parameters maintain their ability to measure an equal time. This is illustrated in FIG. 3, where the wireless devices 10, 12, 14, 22 are sensors 10, 12, 14 and a hub 22. The wireless sensors 10, 12, 14 are part of the wireless MBAN 2. An example of how the wireless devices 10, 12, 14, 22 can communicate with each other are illustrated by drawn lines between the wireless devices. In this example, the sensors 10, 12, 14 can not communicate with the master hub 22. According to the embodiments, a wireless device 10, sensor 10, may be selected as the new master. Data transfer may then be made from the sensor 10 communicating with a second network 30, and this is illustrated by the broken line, for example by long range communication.

In a situation where one sensor loses its short range connection to the master, but other sensors are still able to communicate via short range with the master and hear the sensor data from the lost sensor, it is possible to stream lost sensor data through another sensor. This kind of situation may occur, for example, when one sensor is under the patient or a heating blanket. A lost sensor can also transfer data through backup communication, for example by using long range communication, straight to the infrastructure. This is illustrated in FIG. 4, where the wireless devices 10, 12, 14, 22 are sensors 10, 12, 14 and a hubs 22. The wireless devices are part of the wireless MBAN 2. An example of how the wireless devices 10, 12, 14, 22 can communicate with each other are illustrated by drawn lines between the wireless devices. In this example, the sensor 14 can not communicate with the hub 22. The disclosed embodiments solve this by routing data from the sensor 14 to the hub 22 via one or more other sensors 10, 12, for example by using short range communication. The master, hub 22, can communicate with a second network 30 and this is illustrated by the broken line.

According to at least one embodiment, it is possible, just by adding battery capacity, to use the existing wireless devices of the wireless MBAN to enable short patient transfers without extra devices. When all devices know their wireless MBAN it is possible to associate a new device with any other device included in the wireless MBAN, enabling sharing the new member association data to other devices. Sensors in the same wireless MBAN can share measured data (heart rate etc.) or use body coupled communication to ensure that all sensors connected to one patient, belong to the same MBAN.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for managing wireless devices in a wireless medical body area network (MBAN), comprising:
   configuring the wireless MBAN based on all wireless devices of the wireless MBAN comprising at least one sensor and at least one hub, the configuring comprising sharing at least identification data, battery status, and communication performance between all wireless devices of the wireless MBAN such that every wireless device of the wireless MBAN receives the identification data, battery status, and communication performance of all other wireless devices of the wireless MBAN;
   configuring each of at least a first wireless device and a second wireless device of the wireless MBAN to communicate with the other wireless devices of the wireless MBAN using at least a short range communication protocol and to communicate with a second network using a long range communication protocol;
   configuring the first wireless device of the wireless MBAN as a master of the wireless MBAN depending on the battery status and the communication performance of the first wireless device, wherein only the master communicates with the second network using the long range communication protocol and the other wireless devices not the master do not communicate via the long range communication protocol so as to consume less energy;
   selecting the second wireless device of the wireless MBAN as a new master if the battery status or communication performance of the first wireless device drops below a predefined level; and
   wherein each of the at least the first wireless device and the second wireless device performs a new master calculation to select the new master within the wireless MBAN depending on the battery status and communication performance of each wireless device of the wireless MBAN so as to route data transfer within the wireless MBAN depending on the battery status and communication performance of the wireless devices of the wireless MBAN.

2. The method according to claim 1, wherein the at least one hub is a sensor.

3. The method according to claim 1, wherein the master uses a wired network to communicate with the second network via the long range communication protocol.

4. The method according to claim 1, wherein the wireless devices communicate between each other only using the short range communication protocol.

5. The method according to claim 1, the method comprising configuring the at least one hub with a larger battery capacity compared with each sensor of the MBAN, wherein the first wireless device is the hub.

6. The method according to claim 1, wherein configuring the first wireless device of the wireless MBAN as the master of the wireless MBAN depending on the battery status and the communication performance, comprises selecting the wireless device that has the best battery status and communication performance.

7. The method according to claim 1, wherein a wireless device, which cannot communicate directly with the master, communicates via one or more wireless devices of the wireless MBAN with the master.

8. A wireless medical body area network (MBAN), comprising:
   a plurality of wireless devices comprising at least one sensor and at least one hub; the plurality of wireless devices being configured to share at least identification data, battery status, and communication performance between the plurality of wireless devices of the wireless MBAN such that every wireless device of the wireless MBAN receives the identification data, battery status, and communication performance of all other wireless devices of the wireless MBAN;

each of the plurality of wireless devices being configured to communicate via both a short range communication protocol and a long range communication protocol; the hub being initially configured as a master, wherein the master communicates via both the short range communication protocol and the long range communication protocol and the plurality of wireless devices not the master do not communicate via the long range communication protocol so as to consume less energy; and each of the plurality of wireless devices being configured for routing data within the wireless MBAN and wherein each of the plurality of wireless devices performs a new master calculation to select a new master within the wireless MBAN depending on the battery status and communication performance of each wireless device of the wireless MBAN.

9. The wireless MBAN according to claim 8, wherein the at least one hub is a sensor.

10. The wireless MBAN according to claim 8, wherein the master is configured for communicating with a second network.

11. The wireless MBAN according to claim 10, wherein the long range communication protocol is a wireless protocol and wherein the master is configured to use the long range wireless communication protocol to communicate with the second network.

12. The wireless MBAN according to claim 10, wherein the master is configured to use wired network to communicate with the second network via the long range communication protocol.

13. The wireless MBAN according to claim 8, wherein the wireless devices are configured to communicate between each other only using the short range communication protocol.

14. The wireless MBAN according to claim 8, wherein the at least one hub has a larger battery capacity compared with the battery capacity of each of the plurality of wireless devices.

15. The wireless MBAN according to claim 8, wherein a wireless device, which cannot communicate directly with the master, is configured to communicate via one or more wireless devices of the wireless MBAN with the master.

* * * * *